(12) United States Patent
Shi et al.

(10) Patent No.: US 11,434,467 B2
(45) Date of Patent: Sep. 6, 2022

(54) ASPERGILLUS NIGER SEED CONTINUOUS CULTURE AND METHOD FOR PRODUCING CITRIC ACID THEREFROM

(71) Applicants: Jiangsu Guoxin Union Energy Co., Ltd, Jiangsu (CN); JIANGNAN UNIVERSITY, Jingsu (CN)

(72) Inventors: Guiyang Shi, Jiangsu (CN); Zhijie Hu, Jiangsu (CN); Youran Li, Jiangsu (CN); Xiaodong Jiang, Jiangsu (CN); Sai Jin, Jiangsu (CN); Fuxin Sun, Jiangsu (CN); Cheng Zhang, Jiangsu (CN); Dongjiao Zhou, Jiangsu (CN); Jiawei Lu, Jiangsu (CN); Maodong Miao, Jiangsu (CN); Zihao Fan, Jiangsu (CN)

(73) Assignees: Jiangsu Guoxin Union Energy Co., Ltd, Jiangsu (CN); JIANGNAN UNIVERSITY, Jiangsu (CN)

( * ) Notice: Subject to any disclaimer, the term of this patent is extended or adjusted under 35 U.S.C. 154(b) by 342 days.

(21) Appl. No.: 16/467,990

(22) PCT Filed: Dec. 24, 2018

(86) PCT No.: PCT/CN2018/123053
§ 371 (c)(1),
(2) Date: Jun. 10, 2019

(87) PCT Pub. No.: WO2020/042481
PCT Pub. Date: Mar. 5, 2020

(65) Prior Publication Data
US 2020/0231929 A1 Jul. 23, 2020

(30) Foreign Application Priority Data
Aug. 28, 2018 (CN) .......................... 201810986196.4

(51) Int. Cl.
C12N 1/14 (2006.01)
C12N 1/04 (2006.01)
C12P 7/48 (2006.01)

(52) U.S. Cl.
CPC ................. *C12N 1/14* (2013.01); *C12N 1/04* (2013.01); *C12P 7/48* (2013.01)

(58) Field of Classification Search
CPC .. C12N 1/14; C12N 1/04; C12N 1/145; C12P 7/48; C12R 2001/685
See application file for complete search history.

(56) References Cited

FOREIGN PATENT DOCUMENTS

| CN | 102250971 | 11/2011 |
| CN | 102409066 | 4/2012 |

(Continued)

OTHER PUBLICATIONS

"International Search Report (Form PCT/ISA/210) of PCT/CN2018/123053," dated May 21, 2019, pp. 1-5.

(Continued)

*Primary Examiner* — Olivia M. Wise
*Assistant Examiner* — Anjali Ajit Hirani
(74) *Attorney, Agent, or Firm* — JCIPRNET

(57) ABSTRACT

Disclosed is an *Aspergillus niger* seed continuous culture method, comprising the steps of: (1) at a startup stage, *Aspergillus niger* spores are inoculated into a seed culture medium to obtain a seed liquid; (2) at a seed continuous culture stage, continuous dispersion treatment is performed on the seed liquid obtained in step (1), continuous culture is performed on the seed liquid obtained by dispersion, and meanwhile, a fresh seed feed medium is replenished; and (3) at a stop stage, the replenishment of the fresh seed feed medium and the dispersion treatment are stopped, continuous culture is performed to obtain a seed liquid, and then the seed liquid is transferred into the fermentation medium for fermentation culture. The method according to the present invention makes breakthrough to solve problems that multicellular filamentous bacteria grow slowly and mycelium pellets are easy to lose in continuous culture, thus fully achieving seed continuous culture.

7 Claims, 1 Drawing Sheet

(56) References Cited

FOREIGN PATENT DOCUMENTS

| CN | 103290070 | | | 9/2013 |
|---|---|---|---|---|
| CN | 103290070 | A | * | 9/2013 |
| CN | 102864082 | B | * | 4/2014 |
| CN | 104087624 | | | 10/2014 |
| CN | 104099253 | | | 10/2014 |
| CN | 104531541 | | | 4/2015 |
| CN | 104099253 | B | * | 7/2016 |
| CN | 109055444 | | | 12/2018 |

OTHER PUBLICATIONS

Yao, Wen-Bing, et al., "Introduction to Biotechnology Pharmacy", with (partial) English translation thereof, China Medical Science and Technology Press, Aug. 2015, pp. 1-6.

Baoshi Wang, et al., "Pellet-dispersion strategy to simplify the seed cultivation of Aspergillus niger and optimize citric acid production", Bioprocess Biosyst Eng., Aug. 29, 2016, pp. 45-53.

Baoshi Wang, et al., "Efficient production of citric acid in segmented fermentation using Aspergillus niger based on recycling of a pellet-dispersion strategy", RSC Advances, Oct. 19, 2016, pp. 105003-105009.

* cited by examiner

ASPERGILLUS NIGER SEED CONTINUOUS CULTURE AND METHOD FOR PRODUCING CITRIC ACID THEREFROM

CROSS-REFERENCE TO RELATED APPLICATION

This application is a 371 of international application of PCT application serial no. PCT/CN2018/123053, filed on Dec. 24, 2018, which claims the priority benefit of China application no. 201810986196.4, filed on Aug. 28, 2018. The entirety of each of the above mentioned patent applications is hereby incorporated by reference herein and made a part of this specification.

TECHNICAL FIELD

The present invention relates to the technical field of microbial culture, and in particular to an *Aspergillus niger* seed continuous culture and a method for producing citric acid therefrom.

BACKGROUND

Citric acid is an organic acid with the largest production and usage in the world, and is an important chemical product having widespread applications. The citric acid is mainly used in the food industry, such as sour agent, antioxidant, gelling agent and the like, has broad application prospects in industrial fields, such as medicine, fodder, chemical industry, electronic industry and textile, and the market demand is increasing year by year. As the largest citric acid production and export country, China has advanced production technology, strong market competitiveness, and in particular, ranks top in the world with its creative deep submerged fermentation indexes of starchy raw materials, such as corn and dried sweet potato.

Although the biological fermentation technology has been developing rapidly and novel fermentation technology has come forth continuously in recent years, a plurality of high-efficiency continuous culture modes have been widely applied to different fermentation products, however, due to the fact that the citric acid producing strain, *Aspergillus niger*, belongs to multinucleate filamentous fungus, and has growth characteristics and thallus morphologies totally different from unicellular microorganisms, such as yeast and bacteria, the high-efficiency mature fermentation modes taking yeast and bacteria as the producing strains cannot well applied to the citric acid fermentation production with *Aspergillus niger*, and thus the development of citric acid fermentation industry taking filamentous fungus as the producing strain has been seriously restricted.

Currently, citric acid fermentation production still follows a traditional manner, that is, a large number of *Aspergillus niger* spores are prepared first; the spores are inoculated into a seed culture medium to be cultured to obtain a mature seed solution; and then the remaining seed liquid is transferred into a fermentation medium to be fermented to obtain a citric acid fermentation liquid. The traditional fermentation mode of citric acid has the following problems:

(1) Cumbersome, long-cycle and low-efficiency preparation of *Aspergillus niger* spores: the *Aspergillus niger* strain needs to be subjected to rejuvenation, flat plate screening and three-stage propagation, and the preparation period thereof exceeds 30 days; the manual operation is cumbersome, and the bacterial contamination risk is high.

(2) Poor strain stability and consistency: the current spore preparation mechanization degree is low, the bran koji culture container is small, the consistency in different containers is poor, and as a result, the seed culture quality and the fermentation result are unstable.

(3) Low seed culture efficiency: it takes a germination time of 8-12 hours to inoculate spores into seed culture, and thus the utilization efficiency of the seed tank is reduced.

(4) Unstable seed batch intermittent culture: in batch culture, the thallus growth environment (such as, sugar concentration, pH, and the like) is changing constantly, so that the thallus cannot grow in an optimal environment for a long time.

Currently, there is no continuous culture method for filamentous bacterium seeds in the industry, and the reason is that the filamentous bacteria are generally multi-cells, the growth is slow, blocks and balls are formed, and cells are easily lost in continuous culture. The common continuous culture mainly focuses on the aspects of microorganisms such as bacteria, yeast and the like, all of which are single cells, simple in morphology and easy to control. The patent CN201410329652.X discloses a citric acid *Aspergillus niger* seed continuous culture method based on mycelium pellet dispersion technology, although such a method is referred to as "continuous" culture, the essence of the method is a circulating culture, and the method is to inoculate the previous batch of remaining dispersed mycelia into a new seed culture medium to culture seed liquid so as to achieve circulating culture of seeds. The method reduces usage amount of spores and saves the germination time of spores; however, the seeds need to be in different tanks for switching culture, the device system is increased, and operation is relatively cumbersome; In addition, each batch of seed liquid is still subjected to batch intermittent culture, the culture environment is changing constantly, the seeds cannot be guaranteed to grow under the optimal environment condition; not only is unstable among batches, and more importantly, degeneration of strains easily occurs, and the fermentation level will be influenced. Therefore, there is no seed continuous culture method in a true sense in the current industry.

Compared with the batch intermittent culture in the patent CN201410329652.X, the *Aspergillus niger* seed continuous culture needs to overcome the following technical difficulties: (1) the thalli grow slowly; the mycelium pellets are easy to lose; (2) how to reduce the passage numbers of the strains, and avoid degradation of thalli; (3) how to determine the proper residence time of the seed liquid, avoid thalli from losing too fast, and meanwhile guarantee the quantity of thalli in seed transferring seed liquid is sufficient and the culture environment is stable; (4) how to determine the appropriate size of mycelia, so that the growth rate and the dilution rate of the thalli can achieve a balance.

Therefore, it is a problem needs to be solved urgently in current citric acid production that how to break through limitation of multi-cellular filamentous bacteria, improve the preparation process of seed liquid, reduce usage amount of spores and meanwhile improve the seed culture efficiency, keep seed growth environment maintain in an optimal state, feedback and adjust the culture environment in real time according to the growth state of the thallus, avoid strain degradation, ensure the quality of the seed liquid to be stable, and improve the fermentation level.

SUMMARY

In view of the above problems existing in the prior art, the applicant of the present invention provides an *Aspergillus* niger seed continuous culture and method for producing citric acid therefrom. The method according to the present invention makes breakthrough to solve problems that multicellular filamentous bacteria grow slowly and mycelium pellets are easy to lose in continuous culture, thus fully achieving seed continuous culture, keeping growth environment of the thallus maintain in an optimal state, and avoiding strain degeneration, so that the seed liquid can be in a continuous and stable high-vitality state, and corresponding fermentation indexes can be significantly improved.

The technical solutions of the present invention are described as follows:

There is provided an *Aspergillus niger* seed continuous culture method, comprising the steps of:

(1) at a startup stage, inoculating *Aspergillus niger* spores into a seed culture medium, and culturing for 16~36 h to obtain a seed liquid;

(2) at a seed continuous culture stage, performing continuous dispersion treatment on the seed liquid obtained in step (1), performing continuous culturing on the seed liquid obtained by dispersion, performing fermentation culture after the seed liquid flows out continuously into a fermentation medium in the culturing process, and meanwhile replenishing a fresh seed feed medium at the same rate with the outflow seed liquid;

(3) at a stop stage, stopping the replenishment of the fresh seed feed medium and the dispersion treatment, performing continuous culture to obtain a seed liquid, and then transferring the seed liquid into the fermentation medium for fermentation culture.

The final concentration of the *Aspergillus niger* spores in step (1) after incubation is $1~9\times10^5$ spores/mL; the total sugar of the seed culture medium in step (1) is 100~180 g/L, C/N is 20~40; the seed culture conditions in step (1) are as follows: the temperature is 35~39° C., the air volume is 0.2~0.4 vvm, the tank pressure is 0.05~0.1 Mpa, and the agitation rate is 100~200 rpm.

The total sugar of the fresh seed feed medium replenished in step (2) is 150~200 g/L, C/N is 15~30; the continuous culture conditions in step (2) are as follows: the temperature is 35~37° C., the air volume is 0.3~0.6 vvm, the tank pressure is 0.05~0.07 Mpa, and the agitation rate is 150~200 rpm.

The continuous culture conditions in step (3) are as follows: the temperature is 35~39° C., the air volume is 0.3~0.6 vvm, the tank pressure is 0.05~0.1 Mpa, and the agitation rate is 150~200 rpm.

The continuous dispersion treatment method of the seed liquid in step (2) is to disperse mycelium pellets in the seed liquid into 10~80 m of flocculent hyphae by adopting a disperser.

The replenishing rate of the fresh seed feed medium and the outflow rate of the seed liquid in step (2) are F=V/t, wherein V is the volume of the seed liquid in a seed tank and is determined by different tanks; t is the residence time of the seed liquid, and is adjusted according to cell concentration feedback of the flocculent hyphae, is usually taken a value of 6-24 h.

The fermentation inoculation proportion in step (2) and step (3) is 5~25% (v/v).

The total sugar of the fermentation medium in step (2) and step (3) is 160~200 g/L, C/N is 50~90; the fermentation culture conditions in step (2) and step (3) are as follows: the temperature is 35~39° C., the air volume is 0.1~0.4 vvm, the tank pressure is 0.05~0.1 Mpa, the agitation rate is 100~200 rpm, and the fermentation ends when the concentration of a reducing sugar is less than 5 g/L.

The seed culture medium, the fresh seed feed medium and the fermentation medium are formulated with a starchy raw material liquefying liquid and a nitrogen source respectively; wherein the starchy raw materials at least comprise one of corn flour, cassava flour, sorghum flour and wheat starch; the nitrogen source at least comprises one of ammonium sulfate, urea, soybean meal powder and corn steep liquor.

There is provided a method for producing citric acid, comprising the step of: fermenting the *Aspergillus niger* obtained by the seed continuous culture method to produce citric acid.

The present invention achieves the following beneficial effects:

The method according to the present invention fully achieves seed continuous culture of filamentous bacteria. Compared with the patent CN201410329652.X, the method greatly simplifies the device system, and reduces the usage amount of the seed tank to ⅓; the method also reduces operation steps, significantly improves the production efficiency, saves the seed culture auxiliary time corresponding to each batch of fermentation tank by 12 h; and improves automatic level of seed culture.

Compared with the patent CN201410329652.X, the seed continuous culture method according to the present invention reduces the passage numbers of the strains, effectively avoids the strain degeneration, and keeps continuous running for 15 days while maintains the seed vitality without declining and keeps stable fermentation indexes. By means of efficient continuous running, the start-stop auxiliary time can be shortened, the usage amount of the *Aspergillus niger* spores can be reduced by ⅓, and the culture cost of the *Aspergillus niger* spores can be greatly reduced.

The method according to the present invention has prominent advantages that the thallus is maintained in an optimal growth environment, so that the seeds are always in a continuous and stable high-vitality mature state, and the stability and consistency of the seed liquid quality can be guaranteed. However, the batch intermittent culture is adopted in the patent CN201410329652.X, the pH in the tank is decreased continuously and nutrient substances are gradually consumed, and the culture conditions are gradually unfavorable for the thallus growth and vitality retention, and thereby, the quality of the seed liquid is affected, differences in quality of the seed liquid among batches are relatively large; a larger defect is that, the seed liquid transferred into the fermentation medium is the dispersed mycelia after treatment of the disperser, which need to restore growth in the early stage of the fermentation tank so as to influence the fermentation indexes. Compared with the patent CN201410329652.X, when the fermentation initial sugar concentration is 16%, the fermentation strength is increased by 27.5%, the fermentation conversion rate is increased by 3.4%, and the fermentation stability is significantly improved.

Additionally, due to the fact that the seed vitality is improved and the acid production rate is increased, as compared with the patent CN201410329652.X, the method according to the present invention has greater advantages under high concentration fermentation conditions, when the fermentation initial sugar concentration is increased to 18%, the fermentation acid production exceeds 18%, the fermentation period is less than 60 h, the fermentation conversion rate exceeds 100%, the fermentation strength is increased by 31.6%, and the fermentation conversion rate is increased by 4.8%. Therefore, the method according to the present invention can fully achieve high concentration, high conversion rate and high efficiency fermentation production of citric acid, and play an important promotion role on the technical improvement in the citric acid industry.

The method for continuous culture of *Aspergillus niger* seeds is realized for the first time by adopting continuous feed coupled continuous dispersion, the optimal residence time and mycelium size are determined, culture parameters of seed culture at different stages are optimized, problems that multi-cellular filamentous bacteria grow slowly and mycelium pellets are easy to lose in continuous culture are solved, seed continuous culture are fully achieved, the thallus is made to maintain an optimal growth environment, strain degeneration is avoided, seed liquid is kept in a continuous and stable high-activity state, and corresponding fermentation indexes are significantly improved.

DETAILED DESCRIPTION

Figures 1, 2:
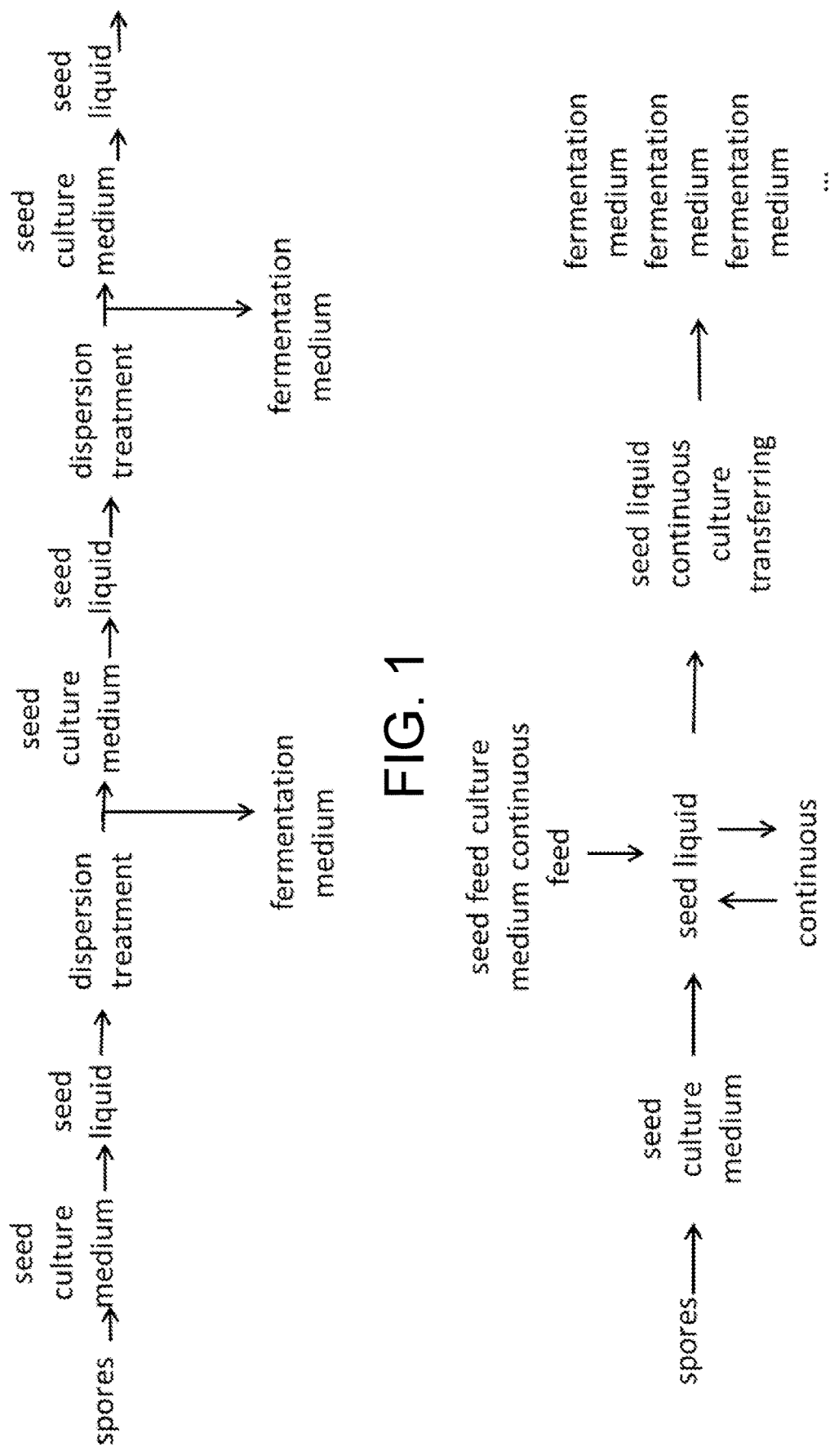
FIG. 1 is a schematic diagram of the culture method according to CN201410329652.X.
FIG. 2 is a schematic diagram of the culture method according to the present invention.

The present invention will be specifically described with reference to the accompanying drawings and examples.

All the raw materials and the reagents involved in the following examples and comparative examples are commercially available; *Aspergillus niger* is from the China Industrial Microbiological Culture Collection Center with the Accession No. CICC 40021. The total sugar and the reducing sugar are both determined with Fehling's titration method, the nitrogen source is determined by Kjeldahl determination, the citric acid assay adopts 0.1429 mol/L NaOH titration, and the spore count adopts blood counting chamber. Unless specially stated, devices and process methods commonly used in the art are employed.

Example 1

Corn flour and tap water were uniformly mixed according to the mass ratio of 1:3, the pH of the slurry was adjusted to 6.0 by $Ca(OH)_2$, and thermostable a-amylase was added in an addition amount of 20 U/g corn flour; ejection liquefaction was carried out, and qualified corn liquefied liquid was obtained after the iodine test was light brown; 80% of the corn liquefied liquid was filtered through a plate frame to remove filter residues to obtain corn syrup.

Startup stage: corn liquefied liquid and ammonium sulfate were formulated into a seed culture medium (total sugar was 100 g/L, C/N was 20), *Aspergillus niger* spores were inoculated into the seed culture medium after sterilized and cooled, and the final concentration of the spores was $9*10^5$ spores/mL, and cultured for 16 h at a temperature of 35° C., an air volume of 0.2 vvm, a tank pressure of 0.05 Mpa, and an agitation rate of 100 rpm to obtain a seed liquid.

Continuous phase: corn liquefied liquid and ammonium sulfate were formulated into a seed feed culture medium (total sugar was 150 g/L, C/N was 15). The obtained seed liquid was performed continuous dispersion treatment to disperse mycelium pellets into 10 m of flocculent hyphae by adopting a disperser; and meanwhile, the speed of continuously replenishing the fresh seed feed medium was controlled with a residence time of 6 h, and the seed liquid flowed out continuously at the same speed into a fermentation medium for fermentation culture. At the seed continuous culture stage, the culture temperature was 35° C., the air volume was 0.3 vvm, the tank pressure was 0.05 Mpa, and the agitation rate was 150 rpm.

Stop stage, when detecting that the seed vitality tends to decline, the replenishment of the fresh seed feed medium and the dispersion treatment were stopped, and then the remaining seed liquid was transferred into the fermentation medium for fermentation culture. The seed culture conditions at this stage: the temperature was 35° C., the air volume was 0.3 vvm, the tank pressure was 0.05 Mpa, and the agitation rate was 150 rpm.

The fermentation medium were formulated with corn liquefied liquid, corn syrup and ammonium sulfate (total sugar was 160 g/L, C/N was 50); the fermentation inoculation proportion was 25% (v/v); the fermentation culture conditions were as follows: the temperature was 35° C., the air volume was 0.1 vvm, the tank pressure was 0.05 Mpa, the agitation rate was 100 rpm, and the fermentation ended when the concentration of a reducing sugar was less than 5 g/L, acidity and residual sugar corresponding to each batch of fermentation were determined, and indexes such as conversion rate and fermentation strength were calculated.

Example 2

Corn flour and tap water were uniformly mixed according to the mass ratio of 1:3, the pH of the slurry was adjusted to 6.0 by $Ca(OH)_2$, and thermostable a-amylase was added in an addition amount of 20 U/g corn flour; ejection liquefaction was carried out, and qualified corn liquefied liquid was obtained after the iodine test was light brown; 80% of the corn liquefied liquid was filtered through a plate frame to remove filter residues to obtain corn syrup. The cassava flour and tap water were uniformly mixed according to the mass ratio of 1:3, the pH of the slurry was adjusted to 6.0 by $Ca(OH)_2$, and thermostable a-amylase was added in an addition amount of 20 U/g cassava flour; ejection liquefaction was carried out, and qualified cassava syrup was obtained after the iodine test was light brown.

Startup stage: corn liquefied liquid and urea were formulated into a seed culture medium (total sugar was 140 g/L, C/N was 30), *Aspergillus niger* spores were inoculated into the seed culture medium after sterilized and cooled, and the final concentration of the spores was $4.5*10^5$ spores/mL, and cultured for 26 h at a temperature of 37° C., an air volume of 0.3 vvm, a tank pressure of 0.075 Mpa, and an agitation rate of 150 rpm to obtain a seed liquid.

Continuous phase: corn liquefied liquid and urea were formulated into a seed feed culture medium (total sugar was 175 g/L, C/N was 23). The obtained seed liquid was performed continuous dispersion treatment to disperse mycelium pellets into 45 m of flocculent hyphae by adopting a disperser; and meanwhile, the speed of continuously replenishing the fresh seed feed medium was controlled with a residence time of 15 h, and the seed liquid flowed out continuously at the same speed into a fermentation medium for fermentation culture. At the seed continuous culture stage, the culture temperature was 36° C., the air volume was 0.45 vvm, the tank pressure was 0.06 Mpa, and the agitation rate was 175 rpm.

Stop stage, when detecting that the seed vitality tends to decline, the replenishment of the fresh seed feed medium and the dispersion treatment were stopped, and then the remaining seed liquid was transferred into the fermentation medium for fermentation culture. The seed culture conditions at this stage: the temperature was 37° C., the air volume was 0.45 vvm, the tank pressure was 0.075 Mpa, and the agitation rate was 175 rpm.

The fermentation medium were formulated with corn liquefied liquid, corn syrup, cassava syrup and urea (total sugar was 180 g/L, C/N was 70); the fermentation inoculation proportion was 15% (v/v); the fermentation culture conditions were as follows: the temperature was 37° C., the air volume was 0.25 vvm, the tank pressure was 0.075 Mpa, the agitation rate was 150 rpm, and the fermentation ended when the concentration of a reducing sugar was less than 5 g/L, acidity and residual sugar corresponding to each batch of fermentation were determined, and indexes such as conversion rate and fermentation strength were calculated.

Example 3

Corn flour and tap water were uniformly mixed according to the mass ratio of 1:3, the pH of the slurry was adjusted to 6.0 by $Ca(OH)_2$, and thermostable a-amylase was added in an addition amount of 20 U/g corn flour; ejection liquefaction was carried out, and qualified corn liquefied liquid was obtained after the iodine test was light brown; 80% of the corn liquefied liquid was filtered through a plate frame to remove filter residues to obtain corn syrup. The wheat starch and tap water were uniformly mixed according to the mass ratio of 1:3, the pH of the slurry was adjusted to 6.0 by $Ca(OH)_2$, and thermostable a-amylase was added in an addition amount of 20 U/g wheat starch; ejection liquefaction was carried out, and qualified wheat syrup was obtained after the iodine test was light brown.

Startup stage: corn liquefied liquid and soybean meal powder were formulated into a seed culture medium (total sugar was 180 g/L, C/N was 40), *Aspergillus niger* spores were inoculated into the seed culture medium after sterilized and cooled, and the final concentration of the spores was $1*10^5$ spores/mL, and cultured for 36 h at a temperature of 39° C., an air volume of 0.4 vvm, a tank pressure of 0.1 Mpa, and an agitation rate of 200 rpm to obtain a seed liquid.

Continuous phase: corn liquefied liquid and soybean meal powder were formulated into a seed feed culture medium (total sugar was 200 g/L, C/N was 30). The obtained seed liquid was performed continuous dispersion treatment to disperse mycelium pellets into 80 m of flocculent hyphae by adopting a disperser; and meanwhile, the speed of continuously replenishing the fresh seed feed medium was controlled with a residence time of 24 h, and the seed liquid flowed out continuously at the same speed into a fermentation medium for fermentation culture. At the seed continuous culture stage, the culture temperature was 37° C., the air volume was 0.6 vvm, the tank pressure was 0.07 Mpa, and the agitation rate was 200 rpm.

Stop stage, when detecting that the seed vitality tends to decline, the replenishment of the fresh seed feed medium and the dispersion treatment were stopped, and then the remaining seed liquid was transferred into the fermentation medium for fermentation culture. The seed culture conditions at this stage: the temperature was 39° C., the air volume was 0.6 vvm, the tank pressure was 0.1 Mpa, and the agitation rate was 200 rpm.

The fermentation medium were formulated with corn liquefied liquid, corn syrup, wheat syrup and soybean meal powder (total sugar was 200 g/L, C/N was 90); the fermentation inoculation proportion was 5% (v/v); the fermentation culture conditions were as follows: the temperature was 39° C., the air volume was 0.4 vvm, the tank pressure was 0.1 Mpa, the agitation rate was 200 rpm, and the fermentation ended when the concentration of a reducing sugar was less than 5 g/L, acidity and residual sugar corresponding to each batch of fermentation were determined, and indexes such as conversion rate and fermentation strength were calculated.

Comparative Example 1 (Example 1 in CN201410329652.X)

Glucose and soybean meal powder were formulated into seed culture medium (the total sugar was 80 g/L, the total nitrogen was 1.5 g/L), and the fermentation medium (the total sugar was 160 g/L, the total nitrogen was 1.5 g/L), respectively; after the seeds were transplanted, the spore concentration was 550,000 spores/mL inoculation; cultured for 20 h to obtain a mature seed solution, seed liquid hyphae were treated by a disperser, mycelium pellets after treatment had an average diameter of 100 μm, and inoculated into the next stage of seed culture medium and the fermentation culture; where the next stage was a fermentation culture, the fermentation ended when the concentration of the reducing sugar in the fermentation culture was reduced to be less than 5 g/L. Such cycles were repeated until the seed viability declined significantly. Acidity and residual sugar corresponding to each batch of fermentation were determined, and indexes such as conversion rate and fermentation strength were calculated.

Comparative Example 2

The fermentation medium had a total sugar of 180 g/L and a total nitrogen of 1.5 g/L); other conditions were the same as in Example 1.

Comparative Example 3

The preparation of corn flour liquefying liquid and corn syrup was the same as in Example 1. Corn liquefied liquid and ammonium sulfate were formulated into a seed culture medium (the total sugar was 120 g/L, the total nitrogen was 2 g/L) and a fermentation medium (the total sugar was 160 g/L, the total nitrogen was 1.0 g/L). *Aspergillus niger* spores were inoculated into the seed culture medium, the final concentration of the spores was $4*10^5$ spores/mL, and cultured for 20 h to obtain a primary mature seed liquid. 70% of the mature seed liquid was transferred into the first batch of fermentation medium for culture and the fermentation ended when the concentration of the reducing sugar was less than 5 g/L. The remaining 30% of the seed liquid was treated by a disperser, the obtained mycelium pellets or fungus blocks with an average diameter of 62 Lm were transferred to the seed culture medium and cultured for 16 h to regain a secondary mature seed liquid. Such cycles were repeated until the seed viability declined significantly. Acidity and residual sugar corresponding to each batch of fermentation were determined, and indexes such as conversion rate and fermentation strength were calculated.

Comparative Example 4

The preparation of corn flour liquefying liquid and corn syrup was the same as in Example 1. Corn liquefied liquid and ammonium sulfate were formulated into a seed culture medium (the total sugar was 120 g/L, the total nitrogen was 2 g/L) and a fermentation medium (the total sugar was 160 g/L, the total nitrogen was 1.0 g/L). *Aspergillus niger* spores were inoculated into the seed culture medium, the final concentration of the spores was $4*10^5$ spores/mL, and cultured for 20 h to obtain a primary mature seed liquid. 70% of the mature seed liquid was transferred into the first batch of fermentation medium for culture and the fermentation ended when the concentration of the reducing sugar was less than 5 g/L. The remaining 30% of the seed liquid was treated by a disperser to obtain mycelium pellets or fungus blocks with an average diameter of 50 m, the fresh seed feed medium were replenished into the remaining seed oil, and cultured for 16 h to regain a secondary mature seed liquid. Such cycles were repeated until the seed viability declined significantly. Acidity and residual sugar corresponding to each batch of fermentation were determined, and indexes such as conversion rate and fermentation strength were calculated.

Comparative Example 5

The speed of continuously replenishing the fresh seed feed medium at the seed continuous culture stage was controlled with a residence time of 4 h; other conditions were the same as in Example 1.

Comparative Example 6

The C/N of the seed feed culture medium at the seed continuous culture stage was 40; other conditions were the same as in Example 1.

Test Example 1

The technical effects of Example 1 and Comparative examples 1, 3 and 4 are compared, as shown in Table 1.

TABLE 1

|  | Example 1 | Comparative example 1 | Comparative example 3 | Comparative example 4 |
|---|---|---|---|---|
| Seed continuous running time (h) | 288 | 260 | 260 | 260 |
| Number of seed tanks | 1 | 3 | 3 | 1 |
| Each batch of seed tank auxiliary time (h) | 0 | 12 | 9 | 1 |
| Bran koji usage amount (barrel/fermentation tank) | 0.22 | 0.33 | 0.33 | 0.33 |
| Number of corresponding fermentation tanks | 18 | 12 | 12 | 12 |
| Corresponding fermentation initial total sugar mean (g/L) | 160 | 160 | 160 | 160 |
| Corresponding fermentation acid production mean (g/L) | 162.5 | 157.0 | 159.0 | 158.5 |
| Corresponding fermentation period mean (h) | 52.5 | 64.7 | 57.2 | 56.6 |
| Corresponding fermentation conversion rate mean (%) | 101.6 | 98.1 | 99.4 | 99.1 |
| Corresponding fermentation strength mean (g/(h · L)) | 3.10 | 2.43 | 2.78 | 2.80 |

A comparison of the technical effects of Example 1 and Comparative examples 1, 3 and 4 shows that: (1) as compared with the patent CN201410329652.X, the method according to the present invention simplifies the device system, and reduces the usage amount of the seed tank to ⅓; the method also reduces operation steps, significantly improves the production efficiency, and saves the seed culture auxiliary time corresponding to each batch of fermentation tank by 12 h. (2) The method according to the present invention has a longer continuous running time, the start-stop auxiliary time can be shortened, the usage amount of the *Aspergillus niger* spores can be reduced by ⅓, and the culture cost of the *Aspergillus niger* spores can be greatly reduced. (3) Compared with the patent CN201410329652.X, when the fermentation initial sugar concentration is 16%, the fermentation strength is increased by 27.5%, and the fermentation conversion rate is increased by 3.4%.

Test Example 2

The technical effects of Example 2 and Comparative example 2 are compared, as shown in Table 2.

TABLE 2

|  | Example 2 | Comparative example 2 |
|---|---|---|
| Seed continuous running time (h) | 360 | 260 |
| Number of seed tanks | 1 | 3 |
| Single seed tank auxiliary time (h) | 34 | 480 |

TABLE 2-continued

|  | Example 2 | Comparative example 2 |
|---|---|---|
| Bran koji usage amount (barrel/fermentation tank) | 0.16 | 0.33 |
| Number of corresponding fermentation tanks | 25 | 12 |
| Corresponding fermentation initial total sugar mean (g/L) | 180 | 180 |
| Corresponding fermentation acid production mean (g/L) | 181.2 | 172.6 |
| Corresponding fermentation period mean (h) | 59.4 | 78.2 |
| Corresponding fermentation conversion rate mean (%) | 100.7 | 95.9 |
| Corresponding fermentation strength mean (g/(h · L)) | 3.03 | 2.30 |

A comparison of the technical effects of Example 2 and Comparative example 2 shows that: as compared with the patent CN201410329652.X, the method according to the present invention has greater advantages under high concentration fermentation conditions, when the fermentation initial sugar concentration is increased to 18%, the fermentation acid production exceeds 18%, the fermentation period is less than 60 h, the fermentation conversion rate exceeds 100%, the fermentation strength is increased by 31.6%, and the fermentation conversion rate is increased by 4.8%. Therefore, the method according to the present invention can fully achieve high concentration, high conversion rate and high efficiency fermentation production of citric acid, and play an important promotion role on the technical improvement in the citric acid industry.

Test Example 3 performances of Example 1 of the present invention and Comparative examples 5 and 6 are compared, as shown in Table 3.

TABLE 3

|  | Example 1 | Comparative example 5 | Comparative example 6 |
|---|---|---|---|
| Seed continuous running time (h) | 288 | 136 | 152 |
| Number of seed tanks | 1 | 1 | 1 |
| Single seed tank auxiliary time (h) | 24 | 24 | 24 |
| Bran koji usage amount (barrel/fermentation tank) | 0.22 | 0.50 | 0.44 |
| Number of corresponding fermentation tanks | 18 | 8 | 9 |
| Corresponding fermentation initial total sugar mean (g/L) | 160 | 160 | 160 |
| Corresponding fermentation acid production mean (g/L) | 162.5 | 158.7 | 157.3 |
| Corresponding fermentation period mean (h) | 52.5 | 55.9 | 58.1 |
| Corresponding fermentation conversion rate mean (%) | 101.6 | 99.2 | 98.3 |
| Corresponding fermentation strength mean (g/(h · L)) | 3.10 | 2.84 | 2.71 |

A comparison of the performances of Example 1 of the present invention and Comparative examples 5 and 6 shows that, when parameters, such as the residence time and C/N of the feed culture medium at the seed continuous culture stage are changed, the seed continuous running time will be significantly affected, the running time will be shortened, seed vitality will be declined rapidly, and the indexes corresponding to fermentation conversion rate and fermentation strength also will be significantly reduced.

The embodiments described above are merely preferred embodiments of the present invention and do not limit the present invention. It can be understood that, any improvement and variation directly derived or conceived by persons skilled in the art without departing from the spirit and concept of the present invention, should be deemed to fall within the protection scope of the present invention.

What is claimed is:

1. An *Aspergillus Niger* seed continuous culture method, comprising the steps of:
   (1) inoculating *Aspergillus Niger* spores into a seed culture medium in a seed tank, and culturing for 16-36 hours to obtain a seed liquid;
   (2) dispersing continuously the seed liquid obtained in step (1), culturing continuously the seed liquid obtained by dispersion, fermenting the seed liquid that flows out continuously into a fermentation medium in a fermentation tank, and replenishing a fresh seed feed medium to the seed tank at the same rate with the outflow seed liquid, wherein the total sugar of the fresh seed feed medium replenished in step (2) is 150-200 g/L, carbon to nitrogen ratio (C/N) is 15-30, and wherein the continuous seed culture conditions in step (2) are as follows: the temperature is 35-37° C., the ratio of volume of air under standard conditions per volume of liquid per minute (VVM) is 0.3-0.6, the tank pressure is 0.05-0.07 Mpa, and the agitation rate is 150-200 rpm, wherein the replenishing rate of the fresh seed feed medium and the outflow rate of the seed liquid in step (2) are F=V/t, wherein V is the volume of the seed liquid in the seed tank, and wherein t is the residence time of the seed liquid and is 6-24 hours; and
   (3) stopping the replenishment of the fresh seed feed medium and the dispersion, maintaining continuous culture to obtain seed liquid, and transferring the seed liquid into the fermentation medium for fermentation culture.

2. The method according to claim 1, wherein the final concentration of the *Aspergillus Niger* spores after step (1) incubation is $1 \times 10^5$ to $9 \times 10^5$ spores/mL, and wherein the seed culture conditions in step (1) are as follows: the total sugar of the seed culture medium is 100-180 g/L, the C/N is 20-40; the temperature is 35-39° C., the VVM is 0.2-0.4, the tank pressure is 0.05-0.1 Mpa, and the agitation rate is 100-200 rpm.

3. The method according to claim 1, wherein the continuous culture conditions in step (3) are as follows: the temperature is 35-39° C., the VVM is 0.3-0.6, the tank pressure is 0.05-0.1 Mpa, and the agitation rate is 150-200 rpm.

4. The method according to claim 1, wherein mycelium pellets in the seed liquid are dispersed in step (2) into 10-80 μm of flocculent hyphae using a disperser.

5. The method according to claim 1, wherein the fermentation inoculation proportion in step (2) and step (3) is 5-25% v/v.

6. The method according to claim 1, wherein the total sugar of the fermentation medium in step (2) and step (3) is 160-200 g/L, C/N is 50-90, and wherein the fermentation culture conditions in step (2) and step (3) are as follows: the temperature is 35-39° C., the VVM is 0.1-0.4, the tank pressure is 0.05-0.1 Mpa, the agitation rate is 100-200 rpm, and fermentation ends when a concentration of a reducing sugar is less than 5 g/L.

7. The method according to claim 1, wherein the seed culture medium, the fresh seed feed medium, and the fermentation medium are formulated with a liquid starchy raw material, and a nitrogen source, wherein the starchy raw material comprises at least one of corn flour, cassava flour, sorghum flour, and wheat starch, and wherein the nitrogen source comprises at least one of ammonium sulfate, urea, soybean meal powder, and corn steep liquor.

* * * * *